United States Patent
Tsuji et al.

(10) Patent No.: US 12,419,825 B2
(45) Date of Patent: Sep. 23, 2025

(54) SURFACE-HYDROPHOBICIZED CELLULOSE NANOFIBERS FOR OILY THICKENER, OILY THICKENER COMPOSITION CONTAINING SAME, COSMETICS AND HYDROPHOBICIZED CELLULOSE NANOFIBER COMPLEX FOR OILY THICKENER CONTAINING SAME, OILY THICKENER COMPOSITION CONTAINING SAME, AND COSMETICS CONTAINING SAME

(71) Applicant: CHUETSU PULP & PAPER CO., LTD., Takaoka (JP)

(72) Inventors: Tsubasa Tsuji, Takaoka (JP); Takashi Nogita, Takaoka (JP)

(73) Assignee: CHUETSU PULP & PAPER CO., LTD., Takaoka (JP)

( * ) Notice: Subject to any disclaimer, the term of this patent is extended or adjusted under 35 U.S.C. 154(b) by 1120 days.

(21) Appl. No.: 16/606,291

(22) PCT Filed: Apr. 18, 2018

(86) PCT No.: PCT/JP2018/015970
§ 371 (c)(1),
(2) Date: Oct. 27, 2021

(87) PCT Pub. No.: WO2018/194080
PCT Pub. Date: Oct. 25, 2018

(65) Prior Publication Data
US 2022/0062149 A1 Mar. 3, 2022

(30) Foreign Application Priority Data
Apr. 19, 2017 (JP) ................................ 2017-083149
Dec. 29, 2017 (JP) ................................ 2017-255108

(51) Int. Cl.
*A61K 8/73* (2006.01)
*A61K 8/02* (2006.01)
*A61Q 19/00* (2006.01)

(52) U.S. Cl.
CPC .............. *A61K 8/731* (2013.01); *A61K 8/027* (2013.01); *A61Q 19/00* (2013.01); *A61K 2800/10* (2013.01); *A61K 2800/413* (2013.01); *A61K 2800/48* (2013.01)

(58) Field of Classification Search
CPC .... A61K 8/731; A61K 8/027; A61K 2800/10; A61K 2800/413; A61K 2800/48; A61Q 19/00; C08B 3/10; C08B 3/08; C08B 3/20; C08B 15/10; C08L 91/00; C08L 1/10; C08H 8/00; C09K 3/00
See application file for complete search history.

(56) References Cited

U.S. PATENT DOCUMENTS

2009/0252800 A1* 10/2009 Wan ........................ C12P 19/04
424/488
2014/0073776 A1 3/2014 Shiramizu et al.

FOREIGN PATENT DOCUMENTS

| CA | 2831897 A1 * | 10/2012 | ............. C08B 15/00 |
| WO | WO-2013031391 A1 * | 3/2013 | ............. B82Y 30/00 |
| WO | WO-2014001874 A1 * | 1/2014 | ............. B65D 65/42 |
| WO | 2016/010016 A1 | 1/2016 | |
| WO | 2017/159823 A1 | 9/2017 | |

OTHER PUBLICATIONS

Loelovich et al., Chapter 9. Nanocellulose—fabrication, structure, properties, and application in the area of care and cure. Book "Fabrication and Self-Assembly of Nanobiomaterials Applications of Nanobiomaterials." vol. 1. 2016. edited by Grumezescu. (Year: 2016).*
Rodionova et al., Surface chemical modification of microfibrillated cellulose: improvement of barrier properties for packaging applications. Cellulose 18(1), 127-134, 2011. (Year: 2011).*
Salas et al., Nanocellulose properties and applications in colloids and interfaces. Current Opinion in Colloid & Interface Science 19 (2014) 383-396. (Year: 2014).*
Pandey et al., Handbook of Polymer Nanocomposites. Processing, Performance and Application. vol. C: Polymer Nanocomposites of Cellulose Nanoparticles. 2015. (Year: 2015).*
Lynnette D. et al., Materials Research For Manufacturing. An Industrial Perspective of Turning Materials into New Products, 2016. (Chapter 9 Nelson et al., American Process: Production of Low Cost Nanocellulose for Renewable, Advanced Materials Applications.) (Year: 2016).*
International Search Report dated Jul. 24, 2018 in International Application No. PCT/JP2018/015970.
International Preliminary Report on Patentability with Translation of the Written Opinion dated Oct. 22, 2019 in International Application No. PCT/JP2018/015970.
H. Sehaqui et al., "Highly Carboxylated Cellulose Nanofibers via Succinic Anhydride Esterification of Wheat Fibers and Facile Mechanical Disintegration", Biomacromolecules, 2017, vol. 18, No. 1, pp. 242-248 (7 pages total).
Matthieu Fumagalli et al., "Versatile Gas-Phase Reactions for Surface to Bulk Esterification of Cellulose Microfibrils Aerogels", Biomacromolecules, 2013, vol. 14, No. 9, pp. 3246-3255 (10 pages total).

(Continued)

*Primary Examiner* — Robert A Wax
*Assistant Examiner* — Ngoc-Anh Thi Nguyen
(74) *Attorney, Agent, or Firm* — Sughrue Mion, PLLC

(57) ABSTRACT

An oil thickener including surface-hydrophobicized CNFs which are cellulose nanofibers having an average thickness of 3 to 200 nm and an average length of 0.1 μm or larger, and a 1 wt. % aqueous dispersion of which has a viscosity of 700 to 2100 mPa·s, and hydroxyl groups in cellobiose units of which are esterified with vinyl esters and/or organic acid esters in a substitution degree of 0.2 to 0.8.

19 Claims, 6 Drawing Sheets

(56) References Cited

OTHER PUBLICATIONS

Yuhong Wang et al., "Aldehyde Functionalized Cellulose Support for Hydrogels", Journal of Applied Polymer Science, 2010, vol. 118, No. 5, pp. 2489-2495 (7 pages total).

* cited by examiner

SURFACE-HYDROPHOBICIZED CELLULOSE NANOFIBERS FOR OILY THICKENER, OILY THICKENER COMPOSITION CONTAINING SAME, COSMETICS AND HYDROPHOBICIZED CELLULOSE NANOFIBER COMPLEX FOR OILY THICKENER CONTAINING SAME, OILY THICKENER COMPOSITION CONTAINING SAME, AND COSMETICS CONTAINING SAME

CROSS-REFERENCE TO RELATED APPLICATIONS

This application is a National Stage of International Application No. PCT/JP2018/015970 filed Apr. 18, 2018, claiming priority based on Japanese Patent Application No. 2017-083149 filed Apr. 19, 2017 and Japanese Patent Application No. 2017-255108 filed Dec. 29, 2017.

TECHNICAL FIELD

The present invention relates to oil thickeners using cellulose fibers, in particular, those which have high viscosity increasing effect on oily ingredients, those which enable oil thickener composition capable of contributing good feeling of use to be obtained, those capable of selectively adsorbing free fatty acids in sebaceous matter, and cosmetics comprising the above oil thickener incorporated therein.)

BACKGROUND ART

Heretofore, as products formulated into a creamy form, gelatinous form, emulsion form or liquid form, compositions have been used which comprise a polymeric material incorporated in a dispersion medium such as water, an alcohol, an oil or the like. The polymeric materials, which are various synthetic polymers, natural polymeric material such as saccharide, have been used to impart increased viscosity to the products.

In recent years, as the polymeric material, cellulose nanofibers (hereinafter often referred to simply as CNFs) have been used which are obtained in such a manner cellulose is nano-fragmented and the resultant is oxidatively modified in part by a chemical treatment, and thickener compositions and the like have been proposed which use such CNFs to exert increased viscosity (see Patent Document 1).

Since silicone oil often used as the oily matter has good spreadability and refreshing feeling, silicone oil is incorporated in various cosmetics including skin care cosmetics, makeup cosmetics and hair cosmetics, and various quasi-drugs. In order to impart increased viscosity to silicone oil or the like, various oil thickeners are used. Cosmetics using an oil thickener include wide variety of products such as a liquid foundation, a sunscreen gel, a moisture cream, a hair gel, an antiperspirant cream and the like. In the present circumstances, however, almost no satisfying oil thickeners are found from the viewpoint of viscosity increasing effect, feeling of use, stability and the like.

Liquid foundations are basically made of a combination of two or three members of a powder, an oily matter and water, and a chemical preparation, an emulsifier, a moisturizer or the like is added thereto according to purposes. Since the powder material present in a makeup film is used with a view to covering skin flaw and a view to attaining a beautiful appearance, it is important for the powder material to remain on a skin over a long period of time in use. In general, however, lowering of a melting point of sebum or the like is caused with the passage of time which is attributable to secretion of unsaturated free fatty acids contained in sebum such as triolein, tripalmitin, oleic acid, palmitic acid and the like. This leads to problems such as makeup deterioration, skin dullness, greasiness of skin, unevenness in makeup and the like.

To cope therewith, an oil thickener having thickening effect on an oily ingredient, and technique for preventing makeup deterioration have been disclosed in published patent documents as described below.

As an invention relating to an thickener for an oily ingredient, patent document 2 discloses, with a view to providing an oil thickener capable of producing an oil thickener composition having high thickening effect on the oily ingredient and excellent feeling of use, and an oily thickener composition comprising the oil thickener and a liquid oily matter, and a cosmetic in which the oil thickener or the oil thickener composition is incorporated, an oil thickener comprising a silicone-modified polysaccharide compound represented by a specific formula and a silicone oil emulsifier.

Further, as an invention for preventing makeup deterioration, patent document 3 discloses complex particles of a core shell type which are spherical resin particles having their surfaces coated with amorphous calcium phosphate such as hydroxyapatite. In this patent document, it is described that the resin particles as core particles yield soft touch and smooth feeling, and the amorphous calcium phosphate coated thereon in a film form effectively adsorb sebum to suppress makeup deterioration and is capable of realizing soft focus (shading off) by light scattering.

However, patent document 1 is silent on the point that the thickener composition disclosed therein increases thickness of silicone oil and the like. Further, although it is described in patent document 2 that the oil thickener has thickening effect on an oily ingredient such as silicone oil, but parent document 2 is silent on thickening effect on an unsaturated free fatty acid. Moreover, patent document 3 provides the complex particles which are incorporated in a cosmetic to prevent makeup deterioration. However, the complex particles per se have no thickening effect on an oily ingredient.

Furthermore, to obtain long-term stability and preservability, it is generally necessary to take supernatant separation in preparations such as cosmetics into consideration. However, these patent documents are silent on supernatant separation in the thickener compositions obtained therein.

PRIOR ART DOCUMENTS

Patent Documents

Patent Document 1: Japanese Unexamined Patent Publication No. 2014-141675
Patent Document 2: Japanese Unexamined Patent Publication No. 2014-218468
Patent Document 3: Japanese Unexamined Patent Publication No. 2010-241785

SUMMARY OF THE INVENTION

Problem to be Solved by the Invention

The present invention has been made in view of the above circumstances. It is, therefore, an object of the present invention to provide an oil thickener which has high viscosity increasing effect on an oily ingredient such as silicone oil, a non-polar organic compound, a low-polarity organic compound or the like and which has good handleability and an oil thickener which has excellent stability and thixotropic rheological properties and which can easily incorporated in a cosmetic.

It is a further object of the present invention to provide an oil thickener having also excellent makeup deterioration inhibiting effect.

It is a still further object of the present invention to provide an oil thickener which is extremely unlikely to cause supernatant separation.

Means to Solve the Problem

The present inventors have made intensive and extensive researches with a view to achieving the above objects. As a result, they have found that use of surface-hydrophobicized CNFs of which hydroxyl groups represent on the surface thereof are substituted in part can solve the above problem. The present invention has thereby been completed.

Further, the present inventors have focused their attention on unreacted hydroxyl groups in the surface-hydrophobicized CNFs and, as a result of intensive and extensive researches, they have found that bulky complexes are obtained by combining compounds having high molecular weights with the surface-hydrophobicized CNFs. Based on the finding, the present invention has been completed.

In other words, the oil thickener of the present invention comprises CNFs having an average thickness of 3 to 200 nm and an average length of 0.1 μm or larger, and a 1 wt. % aqueous dispersion of which has a viscosity of 700 to 2100 mPa·s, and hydroxyl groups in cellobiose units of which are substituted by vinyl esters in a substitution degree of 0.2 to 0.8.

Effect of the Invention

According to the present invention, there are provided an oil thickener which has high viscosity increasing effect on an oily ingredient such as silicone oil, a non-polar organic compound, a low-polarity organic compound or the like and which has good handleability; and an oil thickener which has excellent stability and thixotropic rheological properties and which can easily incorporated in a cosmetic.

Further, an oil thickener having also excellent makeup deterioration inhibiting effect. Is provided. Still further, oil thickener which is extremely unlikely to cause supernatant separation is provided.

MODE FOR CARRYING OUT THE INVENTION

Now, embodiments of the present invention will be described in detail. However, the embodiments will be described by way of specific examples for further understanding. Therefore, the present invention is by no means restricted to the embodiments.

The oil thickener of the present invention makes use of surface-hydrophobicized CNFs of which part of hydroxyl groups present on surfaces of CNFs are substituted.

Further, the oil thickener of the present invention makes use of a bulky hydrophobicized CNF complex obtained in such a manner that hydroxyl groups present on surfaces of CNFs to obtain surface-hydrophobicized CNFs, and compounds having high molecular weights are bonded to hydroxyl groups present on surfaces of the surface-hydrophobicized CNFs and/or in such a manner that CNFs are cross-linked together via the above compounds.

First, a method for preparing CNFs will be described. In the present invention, as the CNFs, there may be mentioned, for example, those derived from polysaccharides including natural plants such as wood fibers (hardwood fibers, softwood fibers), bamboo fibers, sugarcane fibers, seed hair fibers, leaf fibers and the like. These CNFs may be used alone or in combination. As the polysaccharide, it is preferred to use pulp having α-cellulose content of 60 to 99 wt. %. When pulp has such purity that α-cellulose content of 60 wt. % or more, fiber diameter and fiber length are regulated with ease and entanglement between fibers are thereby suppressed, and such pulp has high thermal stability when melted and undergoes no substantial lowering of impact strength and exerts good discoloration inhibitory effect as compared with cases where pulp having α-cellulose content of less than 60 wt. % is used, thereby enhancing the effect of the present invention. On the other hand, if pulp having α-cellulose content of more than 99 wt. % is used, it is difficult to fibrillate pulp fibers to a nano-level.

The CNFs in the present invention are obtained by the fibrillation treatment described below in the form of a CNF dispersion (hereinafter occasionally referred to also as water-containing CNFs).

Figure 1:
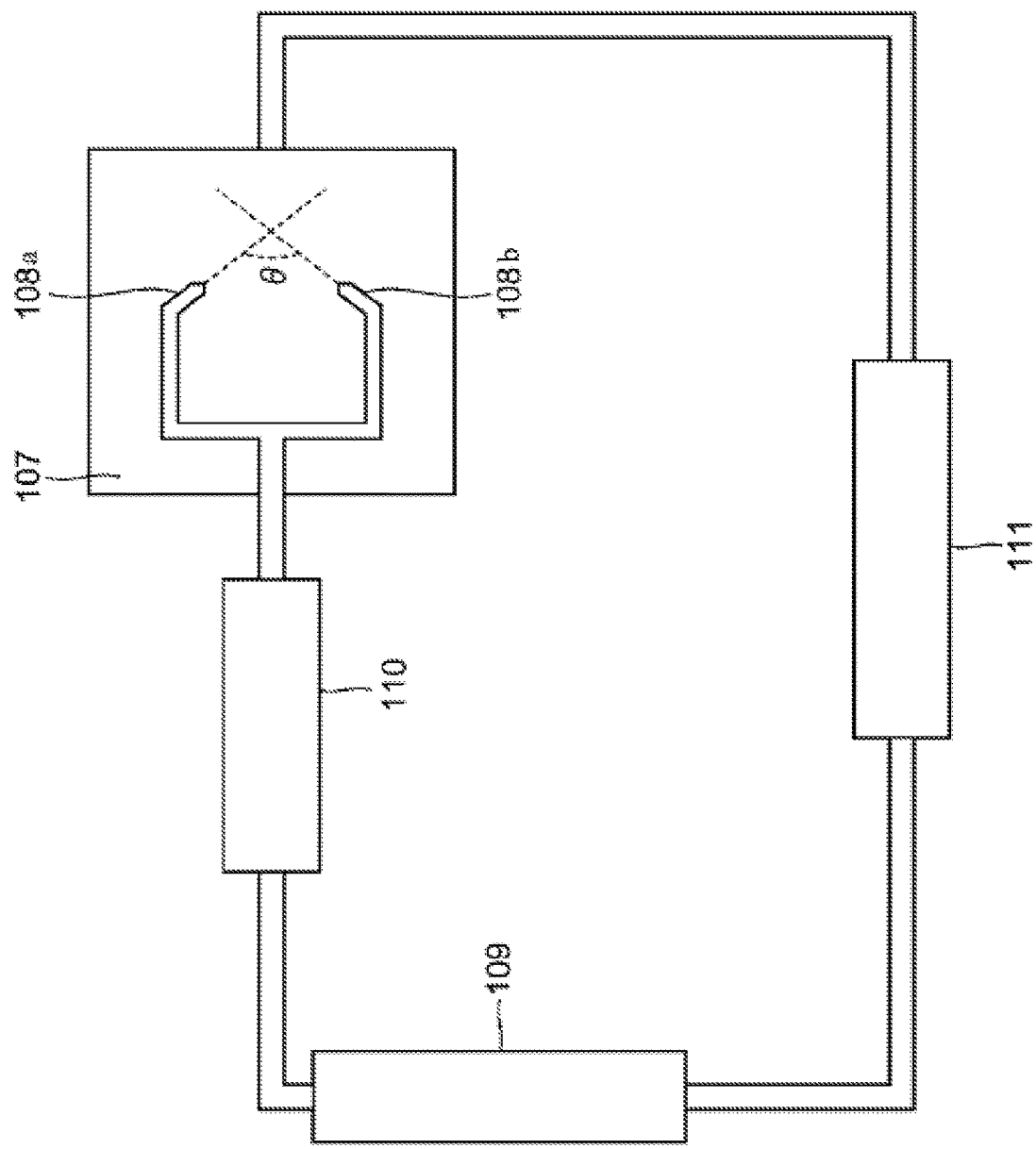
FIG. 1 is a conceptual view of a device for preparing CNFs (device for fibrillation treatment of cellulose)

The fibrillation treatment is carried out by means of an aqueous counter collision method (hereinafter occasionally referred to simply as ACC method) as shown in FIG. 1. This is such a method that pulp suspended in water are introduced into opposing two nozzles (FIG. 1: 108a, 108b) in a chamber (FIG. 1: 107) and jetted from these nozzles toward one point and thereby caused to collide. The device shown in FIG. 1 is of a liquid circulation type and comprises a tank (FIG. 1: 109), a plunger (FIG. 1: 110), opposing two nozzles (FIG. 1: 108a, 108b) and, if desired, a heat exchanger (FIG. 1: 111). In the device, fine particles dispersed in water are introduced into the opposing two nozzles (FIG. 1: 108a, 108b) and jetted from the opposing nozzles (FIG. 1: 108a, 108b) under high pressure to cause the fine particles to counter collide in water.

Figure 2:
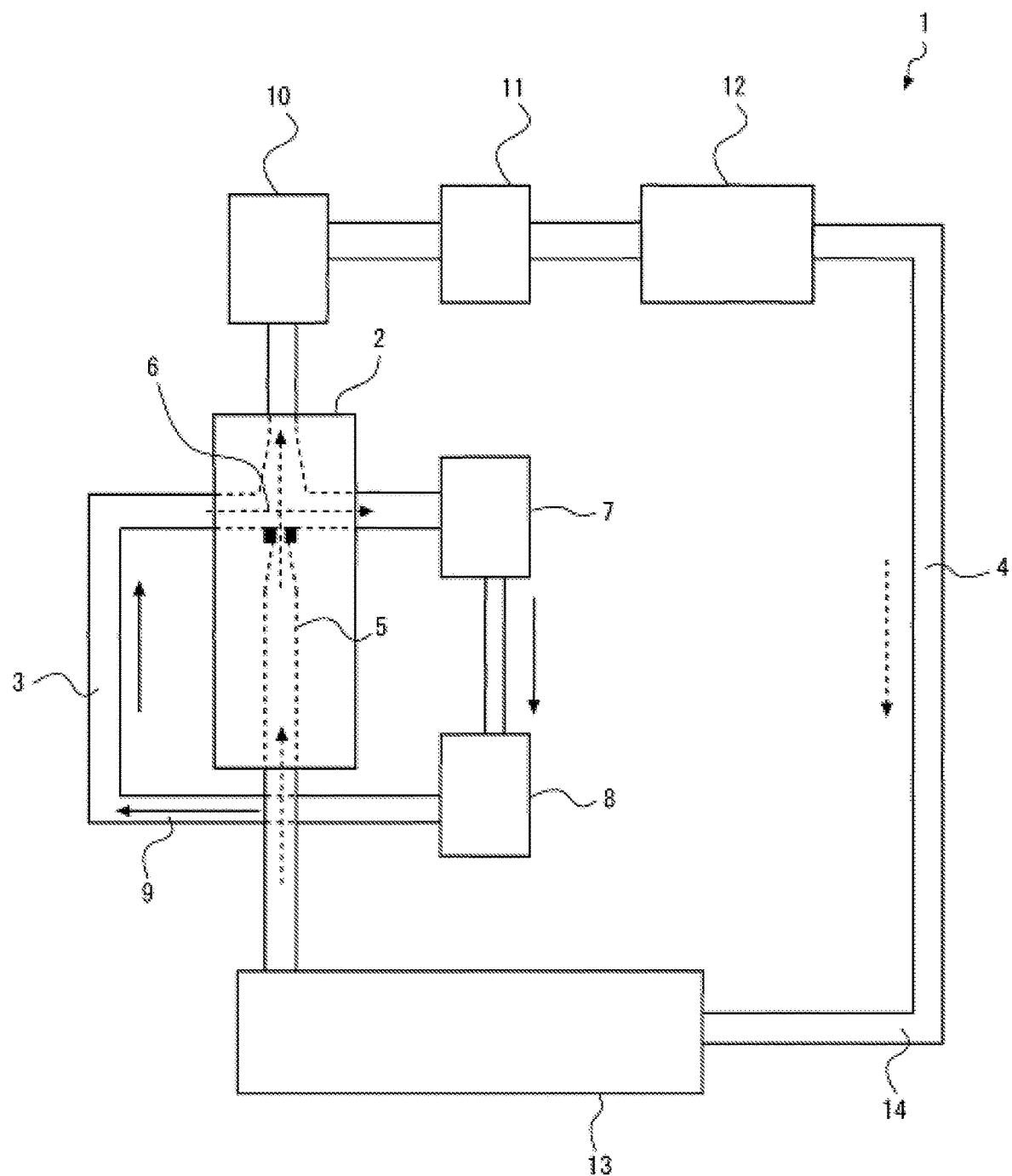
FIG. 2 is a conceptual view of another device for preparing CNFs (device for fibrillation treatment of cellulose)
Figure 3:
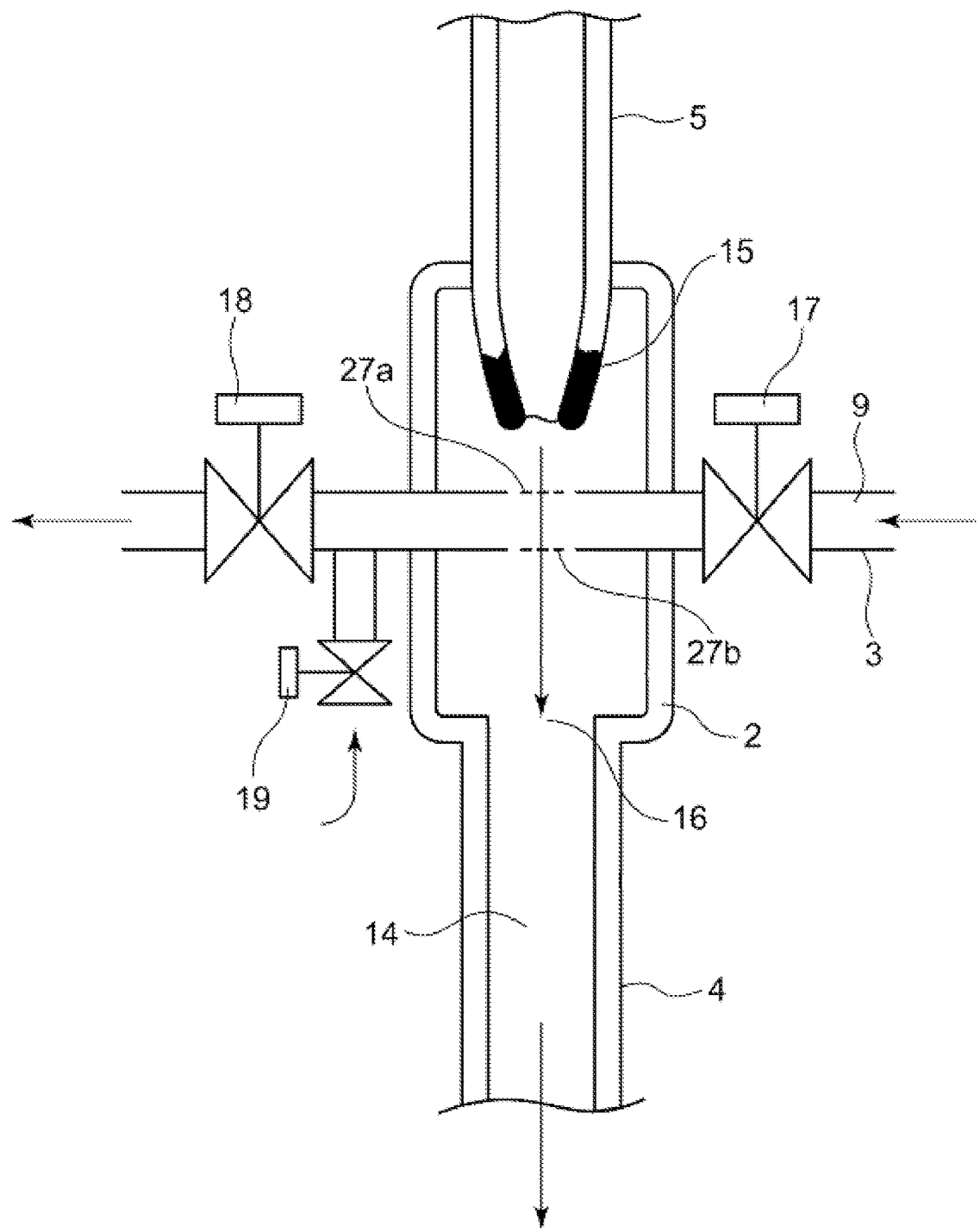
FIG. 3 is a conceptual view showing a part of the device for preparing CNFs (device for fibrillation treatment of cellulose) in FIG. 2 in an enlarged scale.

Prior to carrying out the above described fibrillation treatment, fibrillation treatment may be carried out using a pre-treatment device (see FIGS. 2 and 3). Another fibrillation method may be carried out using such a pre-treatment device. The fibrillation treatment using the pre-treatment device is carried out in such a manner that a highly pressurized water jet with a pressure of about 50 to 400 MPa is caused to collide against a 0.5 to 10 wt. % polysaccharide aqueous mixture. This can be carried out using, for example, the device 1 for preparing CNFs shown in FIG. 2. The device 1 for preparing CNFs comprises a single chamber 2, a polysaccharide slurry supply path 3 as a first fluid medium supply path which is so disposed as to be capable of supplying a polysaccharide slurry to the single chamber 2, and a second fluid medium supply path 4 which permits a non-polysaccharide slurry, for example, water to circulate therein via the single chamber 2. In the single chamber 2, an orifice injection part 5 is provided for orifice-injecting the non-polysaccharide slurry in the second fluid medium supply path 4 in a direction intersecting the direction of polysaccharide slurry supply from the polysaccharide slurry supply path 3. The polysaccharide slurry supply path 3 permits the polysaccharide slurry to be circulated via the single chamber 2.

The polysaccharide slurry supply path 3 and the second fluid medium supply path 4 have a mutual intersection 6 in the single chamber 2.

The polysaccharide slurry supply path 3 is provided with as a polysaccharide supply section and comprises a tank 7 for impounding the polysaccharide slurry and a pump 8 which are disposed in a circulation path 9 as one form of the polysaccharide slurry supply path 3. On the other hand, the second fluid medium supply path 4 functions as a circulation path and comprises a tank 10, a pump 11, a heat exchanger 12, and a plunger 13, which are disposed therein.

The non-polysaccharide slurry is, for example, water and comprehensively means water or a nano-fragmented cellulose slurry containing nano-fragmented polysaccharide a concentration of which increases according to the degree of progress of the operation in such a manner that the water or nano-fragmented polysaccharide slurry is initially water contained in the tank 10 and is then caused to pass through the mutual intersection 6 and return into the tank 10 repeatedly, as the device for preparing a cellulose nanofibers 1 operates, and consequently, develops into a nano-fragmented polysaccharide slurry containing nano-fragmented polysaccharide in such a concentration.

As shown in FIG. 3, the circulation path 9 as one form of the polysaccharide slurry supply path 3 is so disposed as to pass through the camber 2, and an orifice injection opening 14 of an orifice injection part 5 connected to the plunger 13 in the second fluid medium supply path 4 is set to open in the chamber 2 so as to permit the non-polysaccharide slurry to pass across the circulation path 9 by orifice-injecting the non-polysaccharide in a direction intersecting the circulation path 9. An outlet 15 of the chamber 2 is provided at the position opposite to the orifice injection opening 14 in the chamber 2, and the circulation path of the second fluid medium supply path 4 is connected to the outlet 15 of the chamber 2 to constitute the second fluid medium supply path 4.

On the other hand, the circulation path 9 as one form of the polysaccharide slurry supply path 3 is formed using, for example, a vinyl hose, a rubber hose, an aluminum pipe or the like. On the entry side of the circulation path 9 to the chamber 2, a one-way valve 16 is provided which opens only in the direction toward the chamber 2. On the exit side of the circulation path 9 from the chamber 2, a one-way valve 17 is provided which opens only in the discharge direction from the chamber 2. In addition, between the chamber 2 and the one-way valve 17, the circulation path 9 is provided with an air intake valve 18. The air intake valve 18 opens only in the direction of air intake from the outside into the circulation path 9.

According to the above-described device for preparing cellulose nanofibers, the cellulose nanofibers are prepared as follows.

The non-polysaccharide slurry is circulated through the second fluid medium supply path 4 via the chamber 2. Specifically, using the pump 11, the non-polysaccharide slurry in the tank 10 is caused to pass through the heat exchanger 12 and the plunger 13 and thereby circulated in the second fluid medium supply path 4. On the other hand, the polysaccharide slurry is circulated in the polysaccharide slurry supply path 3 via the chamber 2. Specifically, using the pump 8, the polysaccharide slurry in the tank 7 is circulated in the circulation path 9 which is formed using a vinyl hose, a rubber hose or the like.

On the basis of this, the non-polysaccharide slurry circulated in the second fluid medium supply path 4 is orifice-injected against the polysaccharide slurry circulated in the polysaccharide slurry supply path 3 to pass through the chamber 2. Specifically, high pressure water is supplied from the plunger 13 to the orifice injection opening 14 connected to the plunger 13, and the high pressure water is orifice-jetted from the orifice injection opening 14 toward the circulation path 9 under high pressure of about 50 to 400 MPa.

In consequence, the non-polysaccharide slurry passes across, in a direction intersecting the circulation path 9, the inside of the circulation path 9 via a through-hole defined by holes 26a, 26b preliminarily provided in the circulation path 9 which is formed using, for example, a vinyl hose, a rubber hose, an aluminum pipe or the like, while entraining the polysaccharide slurry circulating in the circulation path 9. The non-polysaccharide slurry which has passed across the circulation path 9 rushes toward the outlet 15 of the chamber 2 and enters the second fluid medium supply path 4. The non-polysaccharide slurry is thereby re-circulated in the second fluid medium supply path 4. In the course of repetition of the above process, polysaccharide contained in the polysaccharide slurry circulating in the polysaccharide slurry supply path 3 to pass through the chamber 2 and in the non-polysaccharide slurry circulating in the second fluid medium supply path 4 is gradually fibrillated. Accordingly, a CNF dispersion can be obtained which has a preferable fibrillation degree according to applications and which has high uniformity.

The fibrillation degree from pulp fibers to CNFs can be evaluated from the viscosity value of the CNF dispersion. Specifically, when CNFs contained in the CNF dispersion have an increased fibrillation degree, the CNFs have small fiber lengths, and thus the CNF dispersion has a low viscosity value. Accordingly, the CNF dispersion of which CNFs contained therein have a high fibrillation degree has a low viscosity. On the other hand, a CNF dispersion of which CNFs have a lower fibrillation degree has a high viscosity value because the CNFs contained in such a CNF dispersion have large fiber lengths. Therefore, the CNFs in this CNF dispersion have a lower fibrillation degree as compared with those in the above CNF dispersion.

Further, fiber length to fiber diameter ratios (aspect ratios) of CNFs after fibrillation are different according types of pulp fibers, and hence CNF dispersions resulting from the fibrillation have different viscosity values.

Moreover, viscosities of CNF dispersions can be regulated within a range of about 300 to 10,000 mPa·s, for example, by using different types of pulp fibers in combination or by adjusting the above-described fibrillation degree.

With respect to the CNFs obtained in the above described manner, the nano-fibrillation is effected by cleaving only interaction between the natural cellulose fibers, and hence no substantial structural change of cellulose molecules is caused. The CNFs have a structure represented by Chemical Formula 1 shown below. In other words, the CNFs used in the present invention have 6 hydroxyl groups in its cellobiose unit shown in Chemical Formula 1, and this means that the CNFs chemically unmodified. This can be confirmed by comparing IR spectrum of cellulose with that of CNFs used in the present invention by means of FT-IR. By the ACC method, cellulose fibers can be fragmented to a level of an average particle length of 10 μm, in consequence, CNFs having an average thickness of 3 to 200 nm and an average length of 0.1 μm or larger can be obtained. The average fiber thickness and the average fiber length are determined in such a manner that observation and measurement are carried out on CNFs by means of an appropriately selected scanning electron microscope (SEM), transmission electron microscope (TEM) or the like, and 20 or more of the obtained electron micrographs are selected, and the measured fiber thicknesses and fiber lengths are averaged. On the other hand, in the aqueous counter collision treatment, energy exerted on the cellulose is far smaller than covalent bond dissociation energy (estimated to be one three-hundredth or less), and hence no substantial lowering of polymerization degree of cellulose is caused. The cellulose nanofibers obtained by the ACC method have both hydrophilic sites and hydrophobic sites and exhibit amphipathic properties.

[Chem 1]

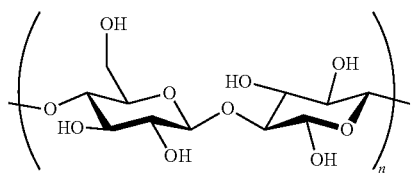

In the present invention, there may be used as CNFs in the present invention, so long as they have hydroxyl groups in their cellobiose units, cellulose nanofibers obtained by another known method for preparing cellulose nanofibers, for example, a method using a chemical treatment such as TEMPO-mediated oxidation, phosphate treatment, ozonation, enzymatic treatment, maleic acid treatment, hydrophobic modification with alkenyl succinic anhydride, hydrophobic modification with alkyl ketene dimer, hydrophobic modification by acetylation or the like; and cellulose nanofibers obtained a known physical method in which cellulosic fibers are fragmented by wet grinding by means of mechanical action of a grinder (millstone type grinder), a disc refiner, a conical refiner or the like (Method for Preparing Surface-Hydrophobicized CNFs)

The method for preparing a surface-hydrophobicized CNFs in the present invention will be described in detail hereinafter.

In this connection, the surface-hydrophobicized CNFs in the present invention means CNFs in which part of hydroxyl groups of cellobiose units are esterified with vinyl esters and/or organic acid vinyl esters.

(Vinyl Estes or Organic Acid Vinyl Esters)

As the vinyl ester or organic acid vinyl ester used in the present invention, there may be mentioned a vinyl ester of a straight-chain or branched chain C2-C20 aliphatic carboxylic acid such as vinyl acetate, vinyl butyrate, vinyl stearate, vinyl laurate, vinyl myristate, vinyl propionate, vinyl versatate or the like, and an aromatic carboxylic acid vinyl ester such as vinyl benzoate or the like.

(Organic Solvent)

As the organic solvent, there may be mentioned a nonionic polar solvent including methylpyrrolidone (hereinafter referred to as NMP), dimethylacetamide (hereinafter referred to as DMAc), dimethylformamide (hereinafter referred to as DMF), dimethyl sulfoxide (hereinafter referred to as DMSO) and the like. When CNFs are dispersed in an organic solvent capable of sufficiently dispersing CNFs, surface modification of cellulose nanofibers can be thereby effected uniformly and efficiently. In particular, DMSO has high CNF-dispersibility and yet is capable of dissolving highly hydrophobic derivatized CNFs. In other words, although substitution of hydroxyl groups in cellobiose units proceeds in various water-containing nonionic polar solvents, the substitution proceeds with highest reaction efficiency when DMSO is used.

(Reaction Conditions, Etc.)

CNFs are dispersed in an organic solvent at such a stirrable concentration that water content in a reaction vessel is about 6% or less, and potassium carbonate is added in an amount in a range of 1 to 40 wt. % relative to the CNFs. Subsequently, a vinyl ester and/or an organic acid vinyl ester is added. The resulting mixture is allowed to react for a time period in a range of several minutes to 5 hours under a temperature of the reaction system of 25° C. to 100° C. After completion of the reaction, the reaction product is collected and dried. By the above reaction process, surface-hydrophobicized CNFs having a substitution degree of 0.2 to 0.8 are obtained. In this connection, although hydrophobicity can sufficiently be imparted to the CNFs even at a water content of about 10%, a smaller water content in the reaction system yields a higher reaction efficiency. Further, potassium carbonate acts as a reaction catalyst, and its buffer effect to keep the reaction system alkaline is important. When its concentration is 40 wt. % or higher, the buffer effect is sufficiently maintained.

(Measurement of Substitution Degree)

In the present invention, measurement of a substitution degree is carried out in the following manner. To 10 ml of a 1% (w/w) surface-hydrophobicized NFC dispersion, an equal amount (10 ml) of an organic solvent is added, and the mixture is dispersed. Subsequently, to the resulting dispersion, a 0.5N sodium hydroxide solution is added in an amount of 10 ml using a whole pipette. The resultant is allowed to react at a temperature of 80° C. for 60 minutes to effect hydrolysis. After passage of the period, the reaction is terminated by cooling. Several drops of a phenolphthalein solution are added thereto. Then, titration with a 0.1N hydrochloric acid is carried out using a burette. From the titration value, the degree of substitution (DS) is calculated.

The surface-hydrophobicized CNFs according to the present invention have thickening effect on the oily ingredient. This is considered to be attributable to the high affinity between alkyl groups derived from the vinyl esters and/or from the organic acid vinyl ester and hydrophobic functional groups such as alkyl groups in the oily ingredient, owing to which the surface-hydrophobicized CNFs and the oily ingredient are well compatible with each other, and the CNFs thereby form a network without aggregating, and in consequence, the viscosity of the oily ingredient is increased.

As the surface-hydrophobicized CNFs according to the present invention, surface-hydrophobicized CNFs having thickening effect on various oily ingredients can be obtained by appropriately selecting fibrillation degree, a kind of the vinyl ester and/or organic acid vinyl ester used for the esterification and substitution degree.

(Method for Preparing Hydrophobicized CNF Complex)

The method for preparing a hydrophobicized CNF complex in the present invention will be described in detail hereinafter.

In this connection, the hydrophobicized CNF complex in the present invention means a complex resulting from such reaction that surface-hydrophobicized CNFs are cross-linked together via a polyhydric alcohol and/or a polyalkylene glycol, and/or a complex resulting from such reaction that a polyhydric alcohol and/or a polyalkylene glycol is bonded to part of hydroxyl groups of surface-hydrophobicized CNFs.

(Vinyl Estes or Organic Acid Vinyl Esters)

As the vinyl ester or organic acid vinyl ester used in the preparation of the hydrophobicized CNF complex, there may be mentioned a vinyl ester of a straight-chain or branched chain C2-C20 aliphatic carboxylic acid such as vinyl acetate, vinyl butyrate, vinyl stearate, vinyl laurate, vinyl myristate, vinyl propionate, vinyl versatate or the like, and an aromatic carboxylic acid vinyl ester such as vinyl benzoate or the like.

(Organic Solvent)

As the organic solvent, there may be mentioned a nonionic polar solvent including methylpyrrolidone (hereinafter referred to as NMP), dimethylacetamide (hereinafter referred to as DMAc), dimethylformamide (hereinafter referred to as DMF), dimethyl sulfoxide (hereinafter referred to as DMSO) and the like. When CNFs are dispersed in an organic solvent capable of sufficiently dispersing CNFs, surface modification of cellulose nanofibers can be thereby effected uniformly and efficiently. In particular, DMSO has high CNF-dispersibility and yet is capable of dissolving highly hydrophobic derivatized CNFs. In other words, although substitution of hydroxyl groups in CNFs proceeds in various water-containing nonionic polar solvents, the substitution proceeds with highest reaction efficiency when DMSO is used.

(Polyhydric Alcohols and Polyalkylene Glycols)

As to the polyhydric alcohol and the Polyalkylene glycol, there is no particular restriction so long as they have two hydroxyl groups or more. As the polyhydric alcohol, there may be mentioned, for example, glycerol, diglycerol, a polyglycerol, ethylene glycol, diethylene glycol, triethylene glycol, propylene glycol, dipropylene glycol, trimethylolpropane, pentaerythritol, 1, 3-butanediol or the like. These may be used alone or in combination. The polyalkylene glycol is a linear polymer compound having a structure with repeated ether bonds in the main chain and, for example, prepared by ring-opening polymerization of a cyclic ether, or the like. As specific examples of the polyalkylene glycol, there may be mentioned a polymer such as polyethylene glycol, polypropylene glycol or the like, and an ethylene oxide-propylene oxide copolymer and a derivative thereof, and the like. As the copolymer, any of copolymers such as a random copolymer, a block copolymer, a graft copolymer, an alternating copolymer and the like may be used.

In this regard, the polyhydric alcohol and the polyalkylene glycol, those having a molecular weight in a range of about 200 to about 10,000 may be used.

(with Respect to Amount of Polyhydric Alcohol and/or Polyalkylene Glycol Relative to CNFs)

It is preferred that the polyhydric alcohol and/or the polyalkylene glycol be bonded to hydroxyl groups contained in cellulose nanofibers having a polymerization degree of about 800 in the ratio of 0.01% to 50%. If the amount of the polyhydric alcohol and/or the polyalkylene glycol is insufficient, bulky hydrophobicized CNF complexes cannot be obtained, and accordingly, CNFs are likely to tightly aggregate together to cause separation between the supernatant and the CNF aggregates. On the other hand, if the amount of the polyhydric alcohol and/or the polyalkylene glycol is superfluous, absolute count of hydroxyl groups in the CNFs is short which are capable of effectively reacting therewith. Accordingly, it is difficult to introduce the polyhydric alcohol and/or the polyalkylene glycol into the hydroxyl groups of the CNFs, and thus, the resultant has poor compatibility with the oily ingredient. Further, since polyalkylene glycol contains many hydrophilic ether bonds, use of excess amount of polyalkylene glycol is contrary to the object of the present invention.

(Cross-Linking Agent)

As to the cross-linking agent in the present invention, there is no particular restriction as long as it is capable of combining hydroxyl groups in cellobiose units contained in cellulose with hydroxyl groups contained in a polyhydric alcohol and/or a polyalkylene glycol. Specifically, as the cross-linking agent, there may be used divinyl esters, isocyanate-based cross-linking agents, and the like.

As the divinyl ester, there may be mentioned, for example, divinyl adipate, divinyl sebacate, diallyl phthalate, diallyl maleate, diallyl succinate, and the like. These may be used alone or in combination.

The isocyanate-based cross-linking agent contains at least a polyisocyanate. As the polyisocyanate compound, there may be mentioned, for example, an aromatic polyisocyanate such as tolylene diisocyanate, diphenylmethane diisocyanate, xylylene diisocyanate or the like, an aliphatic polyisocyanate such as hexamethylene diisocyanate, and an alicyclic polyisocyanate such as isophorone diisocyanate, hydrogenated diphenylmethane diisocyanate, or the like. There may further be mentioned a biuret and isocyanurates thereof, and an adduct as a reaction product thereof with an active hydrogen-containing low molecular compound such as ethylene glycol, propylene glycol, neopentyl glycol, trimethylolpropane, castor oil or the like.

(Reaction Conditions, Etc.)

CNFs are dispersed in an organic solvent at such a stirrable concentration that water content in a reaction vessel is about 6% or less, and potassium carbonate is added in an amount in a range of 1 to 40 wt. % relative to the CNFs. Subsequently, a polyhydric alcohol and/or a polyalkylene glycol, and a cross-linking agent such as a divinyl ester are added in sequence, and then a vinyl ester and/or an organic acid vinyl ester is added. The resulting mixture is allowed to react for a time period in a range of several minutes to 5 hours under a temperature of the reaction system of 25° C. to 100° C. After completion of the reaction, the reaction product is collected, dried and purified to thereby obtain hydrophobicized CNF complexes. In this connection, although hydrophobicity can sufficiently be imparted to the CNFs even at a water content of about 10%, a smaller water content in the reaction system yields a higher reaction efficiency. Further, potassium carbonate acts as a reaction catalyst, and its buffer effect to keep the reaction system alkaline is important. When its concentration is 40 wt. % or higher, the buffer effect is sufficiently maintained.

The hydrophobicized CNF complexes obtained under the above described reaction conditions is bulky in terms of chemical structure, this contributes dispersion stability to enable an oil thickener which is extremely unlikely to cause supernatant separation to be obtained.

The fact that the hydrophobicized CNF complexes according to the present invention are extremely unlikely to cause supernatant separation is considered to be attributable to the following reason. It is considered as the factor causing supernatant separation that adsorption power of an oily ingredient adsorbed by alkyl groups of a vinyl ester modifying surfaces of CNFs is sometimes weaker than adsorption power between hydroxyl groups in the CNFs, and in this case, a CNF network disintegrates with the passage of time and becomes unable to hold the oily ingredient adsorbed on the alkyl groups of the vinyl ester in the surfaces of the CNFs which are present in the CNF network, and consequently, the CNFs approach each other and aggregate to release the oily ingredient as a supernatant. In the hydrophobicized CNF complex of the present invention, however, by virtue of the presence of the polyhydric alcohol and/or the polyalkylene glycol contained in the hydrophobicized CNF complex, distances between CNFs are maintained and thus the oily ingredient adsorbed on the alkyl groups of the vinyl ester remains retained. As a result, the hydrophobicized CNF complex of the present invention is considered to be extremely unlikely to cause supernatant separation.

Therefore, the hydrophobicized CNF complex according to the present invention enables an oil thickener which is extremely unlikely to cause supernatant separation to be obtained by appropriately selecting fibrillation degree of cellulose nanofibers, functional groups; the vinyl esters and/or the organic acid vinyl esters, the polyhydric alcohols and/or the polyalkylene glycols and substitution degree.

In the present invention, the invention of "hydrophobicized CNF complex" and "oil thickener composition" is specified also by method of preparing the same as invention specifying matter. The reason therefor will be described.

The hydrophobicized complex of the present invention includes at least the following two forms.

One form (first form) thereof: a hydrophobicized CNF complex wherein chemically unmodified hydroxyl groups in cellobiose units are esterified with the vinyl ester and/or the organic acid vinyl ester, and two or more hydroxyl groups of the polyhydric alcohol and/or the polyalkylene glycol are bonded to unreacted hydroxyl groups in one of the CNFs and unreacted hydroxyl groups in another of the CNFs.

The other form (second form) thereof: a hydrophobicized CNF complex wherein chemically unmodified hydroxyl groups in cellobiose units are esterified with the vinyl ester and/or the organic acid vinyl ester, and hydroxyl groups of two or more molecules of the polyhydric alcohol and/or polyalkylene glycol are bonded together, and the resultants combines unreacted hydroxyl groups of in the one of the CNFs with unreacted hydroxyl groups in another of the CNFs.

These hydrophobicized CNF complexes coexist in some proportions.

To determine substitution degree of the vinyl ester and/or the organic acid vinyl ester which is ester-bonded to the hydroxyl groups, the ester-bonded vinyl ester and/or organic acid vinyl ester is liberated using a sodium hydroxide solution as described above, and the resultant is subjected titration. From the result of the titration, the substitution degree is calculated. However, if such a process is applied to the hydrophobicized CNF complexes, with respect to the second hydrophobicized CNF complex, the bonds between the molecules of the polyhydric alcohol and/or the polyalkylene glycol are also liberated. This prevents substitution degree of the polyhydric alcohol and/or the polyalkylene glycol from being accurately calculated.

With respect to the present invention, it takes huge expenses and huge amount of time to directly specify the obtained hydrophobicized CNF complexes by their structures or properties, and hence it is practically extremely difficult to unambiguously specify the hydrophobicized CNF complexes by their structures or properties at the time of filing of the application. Accordingly, in the invention of the hydrophobicized CNF complex, the method for preparing the same plays a role as the invention-specifying matter.

Further, in another method for preparing hydrophobicized CNFs, hydrophobicized CNFs are obtained in such a manner that water-containing(CNFs are dispersed in a solvent capable of dispersing water-containing CNFs, trimethoxysilylpropyl isocyanate is added to the dispersion, the resultant is allowed to react at a temperature of 20 to 150° C. for 2 to 10 hours to introduce polysiloxane chains into hydroxyl groups in cellobiose units. In this regard, pyridine may be added as a base catalyst in a small amount.

(Oily Ingredient)

As the oily ingredient used in the present invention for a thickener, there may be mentioned, for example, silicone oil, a non-polar organic compound and a low-polarity organic compound, a higher fatty acid, an ultraviolet absorber, a vegetable oil, a mineral oil, an oil extracted from seeds, an oil obtained by separation, purification and liquefaction of a natural gas or petroleum, a fatty oil obtained from a subcutaneous tissue of an animal, collagen protein hydrolysate obtained by hydrolyzing bones and skins in the presence of an acid, alkali or an enzyme, or a combination thereof, various low-polarity solvents such as benzene, an animal oil or the like.

As the silicone oil, there may be mentioned, for example, a chain polysiloxane (for example, dimethicone, methyl trimethicone, methylphenyl polysiloxane, diphenyl polysiloxane or the like), a cyclic polysiloxane (for example, octamethyl cyclotetrasiloxane, decamethyl cyclopentasiloxane, dodecamethyl cyclohexasiloxane of the like), a silicone resin having a three-dimensional network structure, a silicone rubber, and a modified polysiloxane (for example, an amino-modified polysiloxane, a polyether-modified polysiloxane, an alkyl-modified polysiloxane, a fluorine-modified polysiloxane or the like).

As the non-polar organic compound, there may be mentioned, for example, a liquid paraffin, a light liquid isoparaffin, a heavy liquid isoparaffin, a petroleum jelly, a n-paraffin, an isoparaffin, isododecane, isohexadecane, a polyisobutylene, a hydrogenated polyisobutylene, a polybutene, ozokerite, ceresin, microcrystalline wax, a paraffin wax, a polyethylene wax, a polyethylene/polypropylene wax, squalene, pristane, a polyisoprene or the like.

As the low-polarity organic compound, there may be mentioned, for example, dineopentanoic acid tripropylene glycol, isononyl isononanoate, isopropyl myristate, hexadecyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, acetylated lanolin, isocetyl stearate, isocetyl isostearate, cholesteryl 12-hydroxystearate, ethylene glycol di-2-ethylhexanoate, a dipentaerythritol fatty acid ester, a N-alkyl glycol monoisostearate, neopentyl glycol dicaprate, diisostearyl malate, glycerol di-2-heptylundecanoate, trimethylolpropane tri-2-ethylhexanoate, trimethylolpropane triisostearate, pentaerythrityl tetra-2-ethylhexanoate, triethylhaxanoin (glyceryl tri-2-ethylhexanoate), glycerol trioctanoate, glycerol triisopalmitsate, trimethylolpropane triisostearate, cetyl-2-ethylhexanoate, 2-ethylhexyl palmitate, glycerol trimyristate, glyceride tri-2-heptylundecanoate, castor oil fatty acid methyl ester, oleyl oleate, acetoglyceride, 2-heptylundecyl palmitate, isobutyl adipate, N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, triethyl citrate, and the like.

As the higher fatty acid, there may be mentioned, for example, lauric acid, myristic acid, palmitic acid, stearic acid, behenic acid, oleic acid, undecylenic acid, tolic acid, isostearic acid, linoleic acid, linolenic acid, eicosapentaenoic acid (EPA), docosahexaenoic acid (DHA), and the like.

As the ultraviolet absorber, there may be mentioned a wide range of highly polar oil-based ultraviolet absorbers which are generally used in cosmetics, for example, 2-ethylhexyl 4-methoxycinnamate, 2-hodroxy-4-methoxybenzophenone, a benzoic acid derivative such as para-aminobenzoic acid, a salicylic acid derivative, cinnamic acid derivative, a dibenzoylmethane derivative, a β,β-diphenylacrylate derivative, a benzophenone derivative, a benzylidene camphor derivative a phenylbenzimidazole derivative, a triazine derivative, a phenylbenzotriazole derivative, an anthranil derivative such as methyl anthranilate, an imidazoline derivative, a benzalmalonate derivative, a 4,4-diarylbutadiene derivative, and the like.

As the vegetable oil, there may be mentioned, for example, meadowfoam oil, safflower oil, castor oil, safflower oil, jojoba oil, sunflower oil, almond oil, sesame oil, canola oil, corn oil, soybean oil, peanut oil, avocado oil, camellia oil, macadamia nut oil, olive oil, coconut oil, palm oil, avocado oil, sasanqua oil, and the like.

(Oil Thickener Composition)

The surface-hydrophobicized CNFs and/or the hydrophobicized CNF complexes of the present invention may be used for an oil thickener composition. In other words, the surface-hydrophobicized CNFs and/or the hydrophobicized CNF complexes obtained by appropriately adjusting fibrillation degree, a kind of functional group or substitution degree may be used alone or in combination as an oil thickener composition. Further, the surface-hydrophobicized CNF and/or the hydrophobicized CNF complex obtained by appropriately adjusting fibrillation degree, a kind of functional group or substitution degree may be used as an oil thickener composition in combination with one or more already known agents such as a thickener, a gelling agent, a hydrophobicized agent, a suspending agent, a dispersion-, thermal- or mechanical-stabilizer, an anticaking agent, a fluidity improver, a dry silica, fused silica particles and the like As examples of applications of the oil thickener composition according to the present invention, a thickener for an oil-based paint and a thickener for a hydrophobic resin may be mentioned. Besides, the oil thickener composition may be used an oil adsorbent, an oil absorbent, and an oil composition for an emulsion to contribute to prevention of deformation, prevention, prevention of runs, or improvement in wear resistance.

The surface-hydrophobicized CNFs and/or the hydrophobicized CNF complex of the present invention is added in an amount of 0.01 to 20%, more preferably 0.1 to 10% relative to the oily ingredient and subjected to dispersion to thereby exert high thickening effect. Further, cosmetics having good feeling of use and stability in which the dispersion is incorporated can be provided. If the surface-hydrophobicized CNFs and/or the hydrophobicized CNF complex of the present invention is added in an amount less than 0.01%, desired thickening effect can not necessarily be attained. On the other hand, if the surface-hydrophobicized CNFs and/or the hydrophobicized CNF complex according to the present invention is added in an amount exceeding 20%, the increment exerts no substantial improvement in thickening effect.

The oil thickener composition of the present invention is added in an amount of 0.01 to 20%, more preferably 0.1 to 10% relative to the oily ingredient and subjected to dispersion to thereby exert high thickening effect. Further, cosmetics having good feeling of use and stability in which the dispersion is incorporated can be provided. If the oil thickener composition of the present invention is added in an amount less than 0.01%, desired thickening effect can not necessarily be attained. On the other hand, if the oil thickener composition of the present invention is added in an amount exceeding 20%, the increment exerts no substantial improvement in thickening effect.

EXAMPLES

The present invention will specifically be described hereinafter with reference to Examples and Comparative Examples. However, the present invention is by no means restricted to the Examples.

Prior to the Examples and Comparative Examples, surface-hydrophobicized CNFs were prepared in the following manner.

(Preparation of Surface-Hydrophobicized CNFs)

Bamboo pulp as a starting material was fibrillated by means of ACC method to obtain 1 wt. % aqueous CNF dispersions having different fibrillation degrees. With respect to these aqueous CNF dispersions, viscosities thereof were measured several times and found to be 1,600 to 2,400 Pa·s (herein after referred to as BB-B) and 640 to 960 Pa·s (herein after referred to as LB-C).

Further, hardwood pulp as a starting material was fibrillated by means of ACC method to obtain 1 wt. % aqueous CNF dispersions. With respect to these aqueous CNF dispersions, viscosities thereof were measured several times and found to be 2,400 to 3,600 Pa·s (herein after referred to as LB-C).

Moreover, softwood pulp as a starting material was fibrillated by means of ACC method to obtain 1 wt. % aqueous CNF dispersions. With respect to these aqueous CNF dispersions, viscosities thereof were measured several times and found to be 3,600 to 5,400 Pa·s (herein after referred to as NB-A).

Conditions in Viscosity Measurement

Viscometer: viscometer of TVB-15 model (manufactured by Toki Sangyo Co., Ltd.)

Rotor: M3 or M4

Measurement Temperature: 25° C.

Number of Rotations: 12 rpm

Subsequently, water-containing CNFs were dispersed in dimethyl sulfoxide (DMSO) and potassium carbonate was added thereto, and then the resultant was allowed to react at a temperature of 80° C. In the case where CNF (BB-C) was used, the reaction times were 1 hour or 3 hours, 1 hour or 3.5 hours and 15 minutes or 1 hour with respect to vinyl propionate, vinyl hexanoate and vinyl and vinyl laurate, respectively. The measurement of degree of substitution (DS) of vinyl propionate was extremely difficult and ultimately impossible. With respect to vinyl hexanoate, degree of substitutions (DS) were 0.26 for the reaction time of 1 hour and 0.73 for the reaction time of 3.5 hours. With respect to vinyl laurate, degrees of substitution (DS) were 0.47 for the reaction time of 15 minutes and 0.64 for the reaction time of 3.5 hours. In the case where (BB-B) was used, with respect to vinyl laurate, degrees of substitutions (DS) were 0.28 for the reaction time of 1 hour and 0.56 for the reaction time of 3 hours. After completion of the reaction, the reaction products were collected and washed and purified with an organic solvent.

Examples 1 to 12

(Evaluation 1 on Dispersibility of Surface-Hydrophobicized CNFs)

A subject material (Hex-CNFs DS: 0.73 or Lau-CNFs DS: 0.64) was added to each oil in a concentration of 0.1 wt. %, the prepared oil mixture was stirred and subjected to ultrasonic treatment for 30 minutes. The dispersibility was visually evaluated with the following evaluation criteria.
Evaluation Criteria ○: dispersed well, Δ: not dispersed well, x: agglomerated
The oils used in Examples are as follows.
Ethylhexyl methoxycinnamate (Uvinul MC-80: manufactured by BASF Japan Ltd.), dimethylpolysiloxane (KF-96-10cs: manufactured by Shin-Etsu Chemical Co., Ltd.), cyclopentasiolixane (CY-5: manufactured by Shin-Etsu Chemical Co., Ltd.), triethylhexanoin (T.I.O.: manufactured by Nissin Oilio Group, Ltd.), cetyl ethylhaxanoate (Salacos 816T: manufactured by Nissin Oilio Group, Ltd.), and a mineral oil (Silkool P-70 manufactured by Moresco Corporation).

TABLE 1

|  | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 |
|---|---|---|---|---|---|---|---|---|---|---|---|---|
| Hex-CNFs(BB-C DS: 0.73) | 0.1 | — | 0.1 | — | 0.1 | — | 0.1 | — | 0.1 | — | 0.1 | — |
| Lau-CNFs(BB-C DS: 0.64) | — | 0.1 | — | 0.1 | — | 0.1 | — | 0.1 | — | 0.1 | — | 0.1 |
| Uvinul MC-80 | 1 | 1 | — | — | — | — | — | — | — | — | — | — |
| KF96 10cs | — | — | 1 | 1 | — | — | — | — | — | — | — | — |
| CY-5 | — | — | — | — | 1 | 1 | — | — | — | — | — | — |
| TIO | — | — | — | — | — | — | 1 | 1 | — | — | — | — |
| Salacos 816T | — | — | — | — | — | — | — | — | 1 | 1 | — | — |
| Silcol P-70 | — | — | — | — | — | — | — | — | — | — | 1 | 1 |
| evaluation of dispersibility | ○ | ○ | x | Δ | x | Δ | ○ | ○ | Δ | ○ | x | x |

The results are shown in Table 1. As shown in Table 1, Hex-CNFs could be dispersed in the three oils (Uvinul MC-80 (Example 1), T.I.O. (Example 7) and Salacos 816T (Example 9)) of the six oils.
On the other hand, Lau-CNFs could not be dispersed in Silcol P-70 (Example 12) of the six oils, but could be dispersed in KF96-10cs and CY-5 which are silicone-based oils, and in Uvinul MC-80 which is considered to be hard to gel.

Examples 13 to 18, and Comparative Examples 1 to 3

(Evaluation 2 on Dispersibility of Surface-Hydrophobicized CNFs)

A subject material (Hex-CNFs DS: 0.73 or Lau-CNFs DS: 0.64) was added to each oil in a concentration of 0.1 wt. %, the prepared oil mixture was stirred and subjected to ultrasonic treatment for 30 minutes. The dispersibility was visually evaluated with the above evaluation criteria. Comparative Examples were carried out in substantially the same conditions as in Examples except that AEROSIL R972 (registered trademark: Nippon Aerosil Co., Ltd.) was used as a subject material.

The oils used in Examples 13 to 18 and Comparative Examples 1 to 3 are as follows. Octamethyltrisiloxane (KF-96L-1cs: manufactured by Shin-Etsu Chemical Co., Ltd.), dimethylpolysiloxane (KF-96-10cs: manufactured by Shin-Etsu Chemical Co., Ltd.), and oleic acid (oleic acid: manufactured by Wako Pure Chemical Corporation)

TABLE 2

|  | Ex. 13 | Ex. 14 | Comp. Ex. | Ex. 15 | Ex. 16 | Comp. Ex. | Ex. 17 | Ex. 18 | Comp. Ex. |
|---|---|---|---|---|---|---|---|---|---|
| Hex-CNFs (BB-C DS: 0.73) | 0.1 | — | — | 0.1 | — | — | 0.1 | 1 | — |
| Lau-CNFs (BB-C DS: 0.64) | — | 0.1 | — | — | 0.1 | — | — | 0.1 | — |
| AerosilR972 | — | — | 0.1 | — | — | 0.1 | — | — | 0.1 |
| KF96L-1cs | 1 | 1 | 1 | — | — | — | — | — | — |
| KF96-10cs | — | — | — | 1 | 1 | 1 | — | — | — |
| oleic acid | — | — | — | — | — | — | 1 | 1 | 1 |
| evaluation of dispersibility | x | Δ | x | x | Δ | Δ | ○ | ○ | ○ |

The results are shown in Table 2. As shown in Table 2, Hex-CNFs could not be dispersed in KF96L-1cs nor KF96-10cs but agglomerated (Examples 13 and 15). On the other hand, with respect to Lau-CNFs, no substantial agglomeration was observed, but Lau-CNFs could be dispersed (Examples 14 and 16). Aerosil R972 could not be dispersed but agglomerated in KF-96L-1cs, and could be dispersed in KF96-10cs (Comparative Example 1 and Comparative Example 2)

Further, with respect to oleic acid, all of the subject materials could be dispersed therein (Examples 17 and 18, and Comparative Example 3).

Examples 19 to 27

(Evaluation 3 on Dispersibility of Surface-Hydrophobicized CNFs)

Each of Lau-CNFs which have different substitution degrees and fibrillation degrees as a subject material was added to each oil in a concentration of 0.1 wt. %, the prepared oil mixture was stirred and subjected to ultrasonic treatment for 30 minutes. The dispersibility was visually evaluated with the above evaluation criteria. In this connection, the same oils were used as in Table 2.

TABLE 3

|  | Ex. 19 | Ex. 20 | Ex. 21 | Ex. 22 | Ex. 23 | Ex. 24 | Ex. 25 | Ex. 26 | Ex. 27 |
|---|---|---|---|---|---|---|---|---|---|
| Lau-CNFs (BB-B DS: 0.28) | 0.1 | — | — | 0.1 | — | — | 0.1 | — | — |
| Lau-CNFs (BB-B DS: 0.56) | — | 0.1 | — | — | 0.1 | — | — | 0.1 | — |
| Lau-CNFs (BB-C DS: 0.64) | — | — | 0.1 | — | — | 0.1 | — | — | 0.1 |
| KF96L-1CS | 1 | 1 | 1 | — | — | — | — | — | — |
| KF96 10cs | — | — | — | 1 | 1 | 1 | — | — | — |
| oleic acid | — | — | — | — | — | — | 1 | 1 | 1 |
| evaluation of dispersibility | ○ | x | x | x | Δ | Δ | ○ | ○ | ○ |

The results are shown in Table 3. As shown in Table 3, the subject material in Example 19 which had a low substitution degree did not particularly precipitate in KF96L-1cs and exerted high dispersibility. On the other hand, the subject materials in Examples 20 and 21 precipitated when allowed to stand overnight. The subject material in Example 19 having the substitution degree lower than those of subject materials in Examples 20 and 21 showed dispersibility higher than those of the subject materials in Examples 20 and 21 having the higher substitution degrees.

With respect to KF96-10cs, the subject material in Example 22 which had a low substitution degree could not be dispersed therein, but those in Examples 23 and 24 which had high substitution degrees could be dispersed therein.

With respect to oleic acid, all of the subject materials in Examples 25 to 27 could be dispersed therein.

Examples 28 to 33 and Comparative Examples 4 and 5

(Evaluation 1 on Viscosity of Surface-Hydrophobicized CNFs)

Samples were prepared wherein Lau-CNFs (BB-B DS: 0.28) or Lau-CNFs (BB-C DS: 0.64) were added in amounts of 2 to 5 wt. % or 3 to 6 wt. % respectively relative to KF96L-1cs (Examples 28 and 29). Further, samples were prepared wherein Aerosil R972 was added instead of the Lau-CNFs in amounts of 9 to 12 wt. % (Comparative Example 4). Each of the samples was shaken and stirred, and then left stand for 5 minutes in a constant-temperature chamber (25° C.), and its viscosity was measured using a B-type viscometer (viscometer of TVB-15 model viscometer manufactured by Toki Sangyo Co., Ltd.), and a rotor No. M3 at a rotation speed of 12 rpm.

Samples were prepared wherein Hex-CNFs (BB-C DS: 0.75), Lau-CNFs (BB-B DS: 0.28) or Lau-CNFs (BB-B DS: 0.56) was added in amount of 2 to 4 wt. % or 3 to 6 wt. % respectively relative to oleic acid (Examples 30 to 33). Further, samples were prepared wherein Aerosil R792 was added instead of those CNFs in amounts of 8 to 11 wt. % (Comparative Example 5). Each of the samples were shaken and stirred, and then left to stand for 5 minutes in a constant-temperature chamber, and its viscosity was measured using a B-type viscometer (viscometer of TVB-15 model viscometer manufactured by Toki Sangyo Co., Ltd.), and a rotor No. M3 at a rotation speed of 12 rpm.

TABLE 4

|  | Comp. Ex. 4 | | | | Ex. 28 | | | | Ex. 29 | | | |
|---|---|---|---|---|---|---|---|---|---|---|---|---|
| Lau-CNFs(BB-B DS: 0.28) | — | | | | 2% | 3% | 4% | 5% | | | | |
| Lau-CNFs(BB-C DS: 0.64) | — | | | | | | | | 3% | 4% | 5% | 6% |
| Aerosil R972 | 9% | 10% | 11% | 12% | — | | | | — | | | |
| KF96L-1CS | 91% | 90% | 89% | 88% | 98% | 97% | 96% | 95% | 97% | 96% | 95% | 94% |
| viscosity 25° C. 12 rpm | Unmeasurable | | | | 9,980 | 21,450 | 50,000 | — | 2,240 | 7,190 | 10,190 | 30,350 |

TABLE 5

|  | Comp. Ex. 5 | | | | Ex. 30 | | |
|---|---|---|---|---|---|---|---|
| Hex-CNFs(BB-C DS: 0.73) | — | | | | 2% | 3% | 4% |
| Aerosil R972 | 8% | 9% | 10% | 11% | — | | |
| oleic acid | 92% | 91% | 90% | 89% | 98% | 97% | 96% |
| viscosity 25° C. 12 rpm | 780 | 1,670 | 3,460 | 15,160 | 7,730 | 20,580 | 41,390 |

TABLE 6

|  | Comp. Ex. 5 | | | | Ex. 31 | | | Ex. 32 | | | Comp. Ex. 33 | | | |
|---|---|---|---|---|---|---|---|---|---|---|---|---|---|---|
| Lau-CNFs(BB-B DS: 0.28) | — | | | | 2% | 3% | 4% | — | | | — | | | |
| Lau-CNFs(BB-B DS: 0.56) | — | | | | | | | 2% | 3% | 4% | — | | | |
| Lau-CNFs(BB-C DS: 0.64) | — | | | | | | | | | | 3% | 4% | 5% | 6% |
| Aerosil R972 | 8% | 9% | 10% | 11% | — | | | — | | | — | | | |
| oleic acid | 92% | 91% | 90% | 89% | 98% | 97% | 96% | 98% | 97% | 96% | 97% | 96% | 95% | 94% |
| Viscosity 25° C. 12 rpm | 780 | 1,670 | 3,460 | 15,160 | 9,980 | 21,450 | 50,000 | 6,210 | 13,240 | 45,130 | 2,240 | 7,190 | 10,190 | 30,350 |

The results are shown in Tables 4, 5 and 6. As shown in Table 4, with respect to Lau-CNFs, thickening effect thereof were confirmed (Examples 28 and 29). With respect to Aerosil R972, the samples became pasty and viscosities thereof were unmeasurable (Comparative Example 4). From the results in Examples 28 and 29, it was found that the Lau-CNFs having the lower substitution degree exerted higher thickening effect on KF96-1cs. Further, as is seen from Tables 5 and 6, about 9 wt. % of Aerosil R972 was required in order to attain thickening effect on oleic acid (Comparative Example 5).

On the other hand, it was found that about 2 wt. % of Hex-CNFs yielded sufficient thickening effect (Example 30). With respect to Lau-CNFs (BB-B DS: 0.28) and Lau-CNFs (BB-B DS: 0.56), it was found that about 2 wt. % thereof yielded sufficient thickening effect (Examples 31 and 32). With respect to Lau-CNFs (BB-C DS: 0.64), about 3 wt. % thereof yielded thickening effect (Example 33). Accordingly, it was found that Hex-CNFs and Lau-CNFs exerted thickening effects on oleic acid even at low concentrations lower than that of Aerosil R972.

Examples 34 to 37 and Comparative Examples 6 to 8

(Evaluation 2 on Viscosity of Surface-Hydrophobicized CNFs)

Samples were prepared wherein Lau-CNFs (BB-C DS: 0.64) was added in amounts of 2 to 5 wt. % relative to KF96L-1cs and 3 to 6 wt. % relative to KF96-10cs (Examples 34 and 35). On the other hand, instead of the Lau-CNFs, Aerosil R972 was added to KF96L-1cs and KF96-10cs in concentrations of 9 to 12 wt. % and 10 to 12 wt. %, respectively, to prepare samples in Comparative Examples 6 and 7. Each of the samples was shaken and stirred, and then left stand for 5 minutes in a constant-temperature chamber (25° C.), and its viscosity was measured using a B-type viscometer (viscometer of TVB-15 model viscometer manufactured by Toki Sangyo Co., Ltd.), and a rotor No. M3 at a rotation speed of 12 rpm.

Samples were prepared wherein Hex-CNFs (BB-C DS:0.73) and Lau-CNFs (BB-C DS: 0.64) are added in concentrations of 2 to 4 wt. % and 3 to 6 wt. % respectively relative to oleic acid (Examples 36 and 37). Instead of Lau-CNFs (BB-C DS: 0.64) and Hex-CNFs (BB-C DS: 0.75), Aerosil R972 was added in concentrations of 8 to 11 wt. % to prepare samples in Comparative Examples 8. Each of the samples was shaken and stirred, and then left stand for 5 minutes in a constant-temperature chamber (25° C.), and its viscosity was measured using a B-type viscometer (viscometer of TVB-15 model viscometer manufactured by Toki Sangyo Co., Ltd.), and a rotor No. M3 at a rotation speed of 12 rpm.

The results are shown in Tables 7 and 8. With respect to KF96L-1cs, Lau-CNFs (BB-AerosilC DS: 0.64) were confirmed to exert thickening effect at concentrations lower than those of Aerosil R972 (Example 34, Comparative Example 6). On the other hand, with respect also to KF96-10cs, Lau-CNFs (BB-C DS: 0.64) were confirmed to exert thickening effect at concentrations lower than Aerosil R972 (Example 35, Comparative Example 7).

Further, as is seen from Table 8, with respect also to oleic acid, both of Lau-CNFs (BB-C DS: 0.64) and Hex-CNFs (BB-C DS: 0.73) were confirmed to exert thickening effect at concentrations lower than those of Aerosil R972 (Examples 36 and 37, Comparative Example 8).

Examples 38 to 42

(Evaluation 3 on Viscosity of Surface-Hydrophobicized CNFs)

Samples were prepared wherein Lau-CNFs (BB-C DS: 0.56) was added in amounts of 2 to 5 wt. % relative to each of oils (ethylhexyl methoxycinnamate (Uvinul MC-80: manufactured by BASF Japan Ltd.), triethylhexanoin (T.I.O.: manufactured by Nissin Oilio Group, Ltd.), and cetyl ethylhaxanoate (Salacos 816T: manufactured by Nissin Oilio Group, Ltd.))(Examples 38 to 40).

Samples were prepared wherein Lau-CNFs (BB-C DS: 0.56) was added in amounts of 3 to 5 wt. % relative to each of oils (dimethylpolysiloxane (KF-96-10cs: manufactured by Shin-Etsu Chemical Co., Ltd.) and cyclopentasiolixane (CY-5: manufactured by Shin-Etsu Chemical Co., Ltd.) (Examples 41 and 42).

Each of the samples was shaken and stirred, and then left stand for 5 minutes in a constant-temperature chamber (25° C.), and its viscosity was measured using a B-type viscometer (viscometer of TVB-15 model viscometer manufactured by Toki Sangyo Co., Ltd.), and a rotor No. M3 at a rotation speed of 60 rpm.

TABLE 7

|  | Comp. Ex. 6 | | | | Comp. Ex. 7 | | | Ex. 34 | | | | Ex. 35 | | | |
|---|---|---|---|---|---|---|---|---|---|---|---|---|---|---|---|
| Lau-CNFs(BB-C DS: 0.64) | — | | | | — | | | 2% | 3% | 4% | 5% | 3% | 4% | 5% | 6% |
| AerosilR972 | 9% | 10% | 11% | 12% | 10% | 1% | 12% | — | | | | — | | | |
| KF96L-1CS | 91% | 90% | 89% | 88% | | | | 98% | 97% | 96% | 95% | | | | |
| KF96 10cs | | | | | 90% | 89% | 88% | | | | | 97% | 96% | 95% | 94% |
| viscosity 25° C. 12 rpm | 5,090 | 6,900 | 5,530 | 5,290 | 8,375 | 19,605 | — | — | 700 | 1,360 | 4,380 | 3,570 | 7,290 | 10,740 | 19,400 |

TABLE 8

|  | Comp. Ex. 8 | | | | Ex. 36 | | | Ex. 37 | | | |
|---|---|---|---|---|---|---|---|---|---|---|---|
| Hex-CNFs(BB-C DS: 0.73) | — | | | | 2% | 3% | 4% | — | | | |
| Lau-CNFs(BB-C DS: 0.64) | — | | | | | | | 3% | 4% | 5% | 6% |
| Aerosil R972 | 8% | 9% | 10% | 11% | — | | | — | | | |
| oleic acid | 92% | 91% | 90% | 89% | 98% | 97% | 96% | 97% | 96% | 95% | 94% |
| viscosity 25° C. 12 rpm | 780 | 1,670 | 3,460 | 15,160 | 7,730 | 20,580 | 41,390 | 2,240 | 7,190 | 10,190 | 30,350 |

TABLE 9

|  | Ex. 38 | | | | Ex. 39 | | | | Ex. 40 | | | |
| --- | --- | --- | --- | --- | --- | --- | --- | --- | --- | --- | --- | --- |
| Lau-CNFs(BB-B DS: 0.56) | 2% | 3% | 4% | 5% | 2% | 3% | 4% | 5% | 2% | 3% | 4% | 5% |
| Uvinul MC-80 | 98% | 97% | 96% | 95% | — | — | — | — | — | — | — | — |
| TIO | — | — | — | — | 98% | 97% | 96% | 95% | — | — | — | — |
| Salacos 816T | — | — | — | — | — | — | — | — | 98% | 97% | 96% | 95% |
| viscisity 25° C. 6 rpm | 8,900 | 23,000 | 45,000 | 74,700 | 6,900 | 12,700 | 27,200 | 66,800 | 2,700 | 8,700 | 19,650 | 47,850 |
| viscosity 25° C. 60 rpm | 1930 | 4590 | 9420 | — | 1,760 | 4,020 | 9,280 | — | 1,230 | 3,710 | 8,285 | — |

TABLE 10

|  | Ex. 41 | | | Ex. 42 | | |
| --- | --- | --- | --- | --- | --- | --- |
| Lau-CNFs(BB-C DS: 0.65) | 3% | 4% | 5% | 3% | 4% | 5% |
| KF96 10cs | 97% | 96% | 95% | — | — | — |
| CY-5 | — | — | — | 97% | 96% | 95% |
| viscisity 25° C. 6 rpm | 6,100 | 14,300 | 43,300 | 7,500 | 16,000 | 44,650 |
| viscosity 25° C. 60 rpm | 1,180 | 2,437 | 7,210 | 1,520 | 3,110 | 7,310 |

The results are shown in Tables 9 and 10. As is seen from Tables 9 and 10, the Lau-CNFs were confirmed to have thickening effect with respect to all of the oils.

Each of Lau-CNFs and Aerosil 200 as an oil thickener was added to oleic acid in such an amount as to prepare an oleic acid dispersion having a viscosity of about 40,000 mPa·s which is close to that of a common gel. With respect to each of these dispersions, flow curves were created (thixotropic evaluation) and yield stresses were measured.

The 6% Lau-CNF-oleic acid dispersion had a viscosity of 33,800 mPa·s, and the 5% Aerosil 200-oleic acid dispersion had a viscosity of 39,500 mPa·s.

Figure 4:
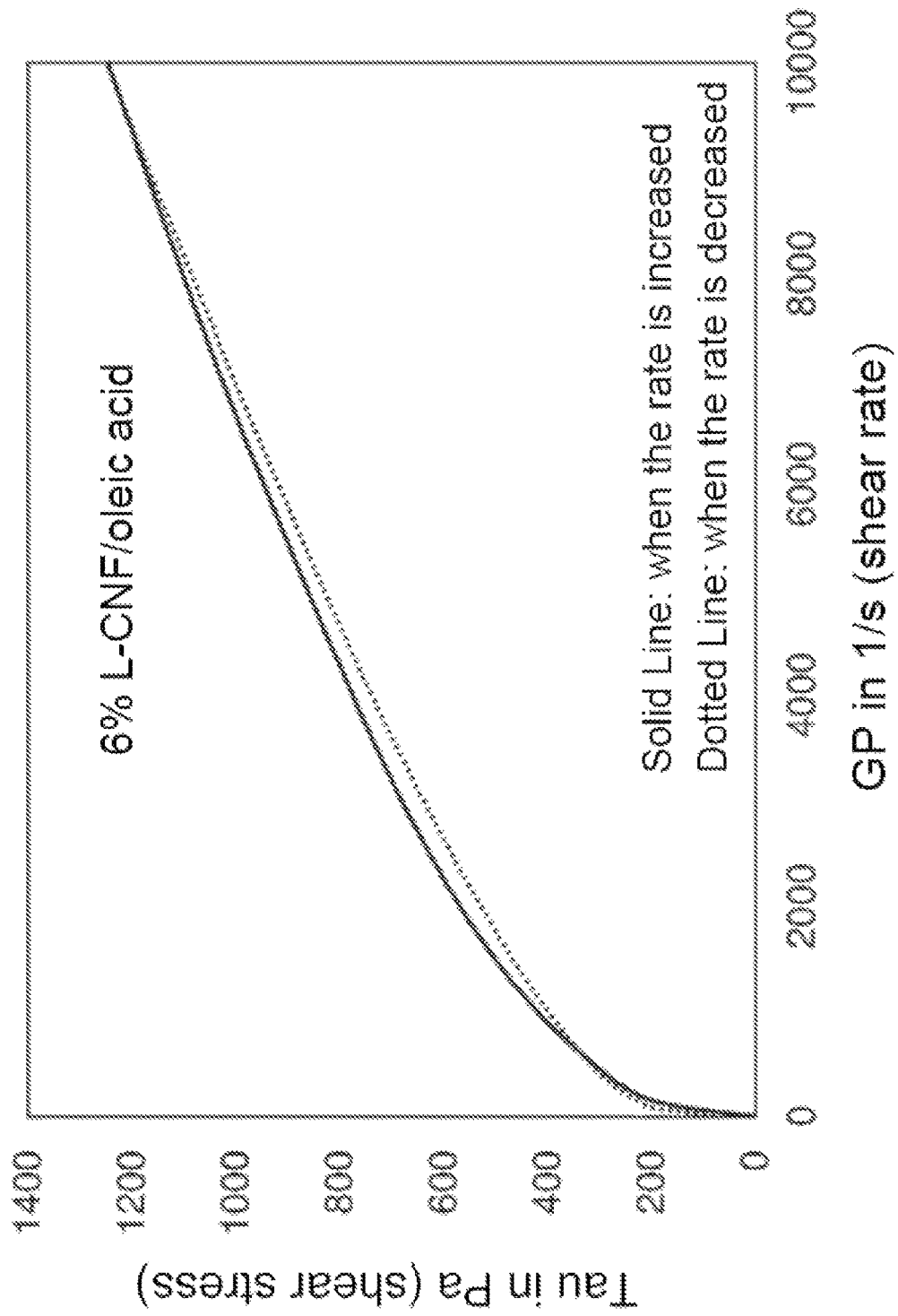
FIG. 4 shows flow curves obtained.
Figure 5:
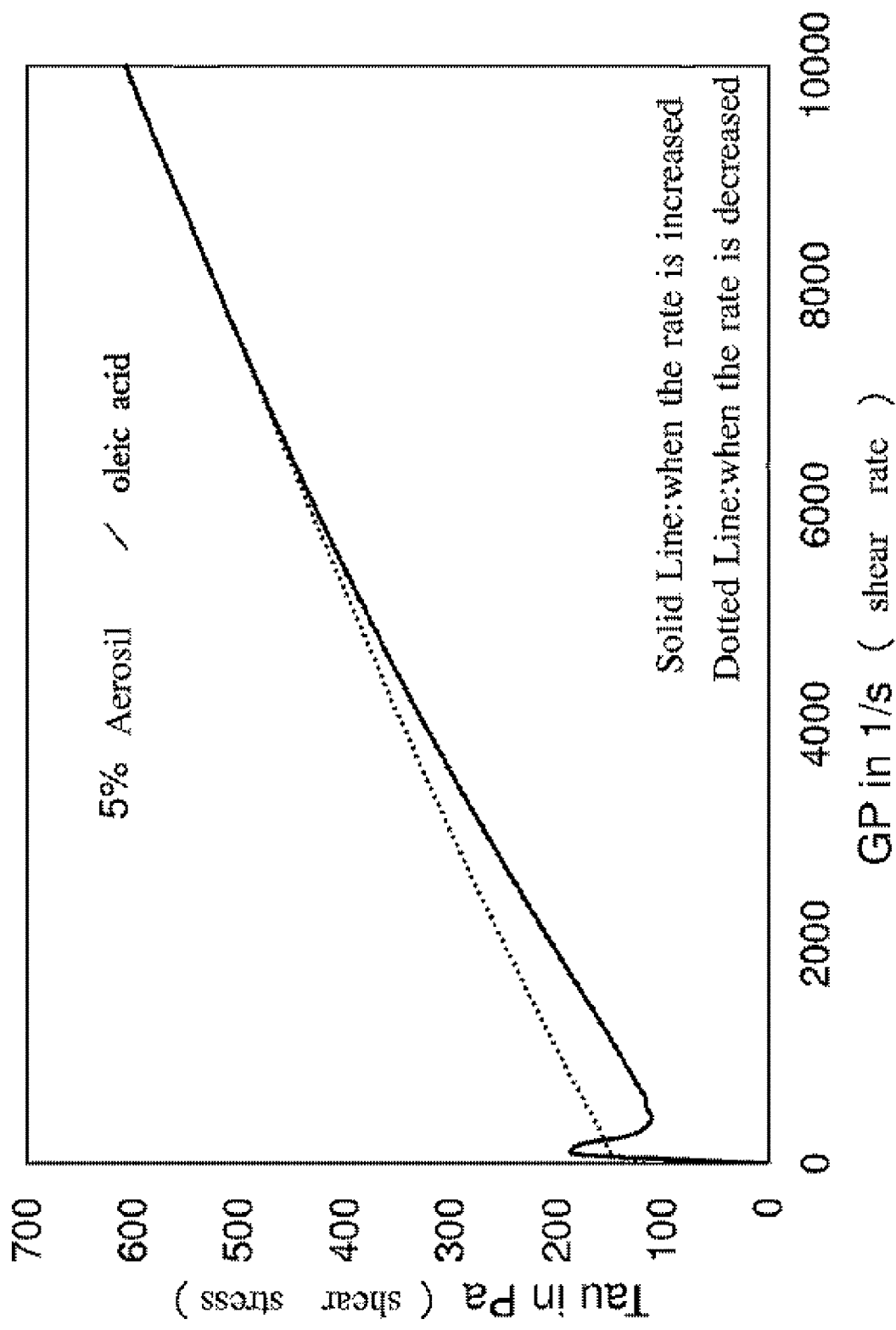
FIG. 5 shows flow curves obtained.
Figure 6:
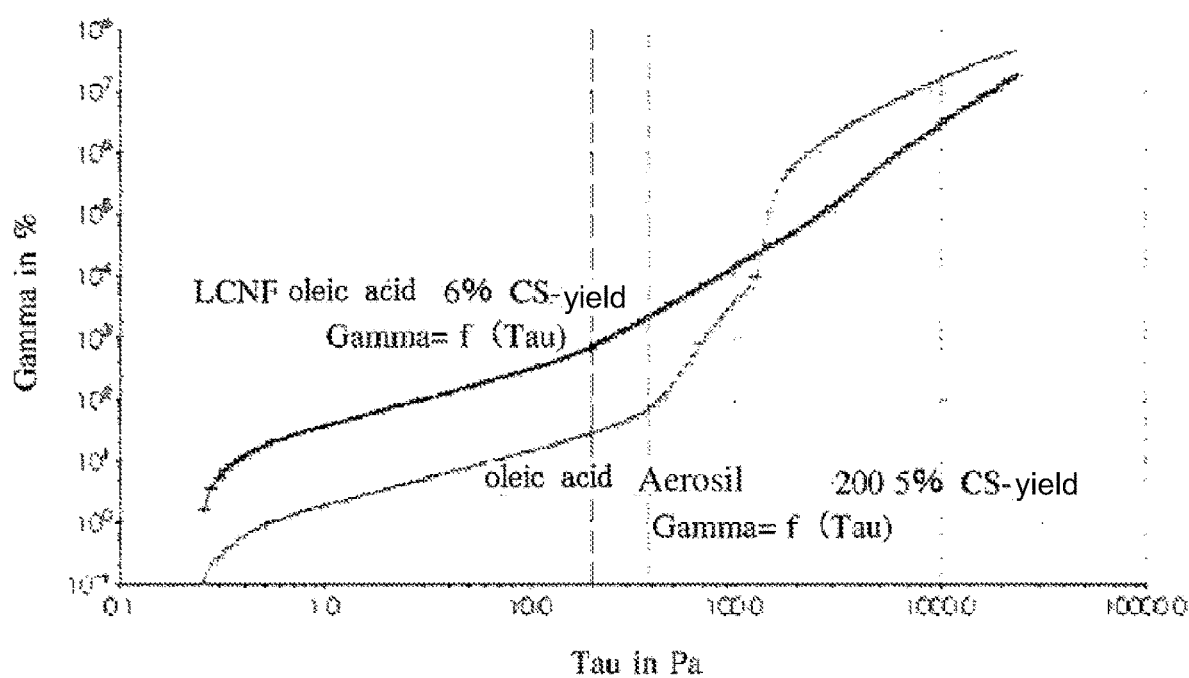
FIG. 6 shows results of yield stress measurement.

The results of the measurements are shown in FIGS. 4, 5 and 6.

As is seen from FIG. 4, the 5% Aerosil 200-oleic acid dispersion showed rheopectic properties. As is seen from FIG. 5, the 6% Lau-CNF-oleic acid dispersion showed a hysteresis loop which is indicative of thixotropic properties.

As is seen from FIG. 6, the 5% Aerosil 200-oleic acid dispersion showed a yield value of 37.70 Pa and the 6% Lau-CNF-oleic acid dispersion showed a yield value of 19.73 Pa.

Example 43

(Preparation of Hydrophobicized CNF Complex)

Bamboo pulp as a starting material was fibrillated by means of ACC method to obtain a 1% CNF aqueous dispersion. Viscosity of the CNF aqueous dispersion was measured and found to be 815 mPa·s (hereinafter referred to as BB-C).

Conditions in Viscosity Measurement
  Viscometer: viscometer of TVB-15 model (manufactured by Toki Sangyo Co., Ltd.)
  Rotor: M3 or M4
  Measurement Temperature: 25° C.
  Number of Rotations: 12 rpm
  Subsequently, water-containing CNFs were dispersed in dimethyl sulfoxide (DMSO) and potassium carbonate was added thereto, and then polyethylene glycol (molecular weight: 20,000), divinyl adipate, an organic acid vinyl (vinyl propionate, vinyl hexanoate, or vinyl laurate) were added in sequence, the resultant was allowed to react at a temperature of 80° C., and the reaction product was washed and purified with methanol (Hex-PEG-CNF BB-C)

(Evaluation on Dispersibility of Surface-Hydrophobicized CNF Complex)

A subject material (Hex-PEG-CNFs) was added to the oil shown in the following in a concentration of 0.1 wt. %, the prepared oil mixture was stirred and subjected to ultrasonic treatment for 30 minutes. The dispersibility was visually evaluated with the following evaluation criteria.

Evaluation Criteria

◯: dispersed well, Δ: not dispersed well, x: agglomerated

The oil used is as follows.

cyclopentasiolixane (CY-5: manufactured by Shin-Etsu Chemical Co., Ltd.)

TABLE 11

|  | Example43 |
| --- | --- |
| Hex-PEG-CNFs(BB-C) | 0.1 |
| CY-5 | 1 |
| evaluation of dispersibility | ◯ |

As is seen from Table 11, although the evaluations of dispersibility were x and Δ in Example 5 and Example 6, respectively, the dispersibility was evaluated as ◯ with respect to the specimen wherein the hydrophobicized CNF complex was used. Further, in the specimen, no supernatant separation was observed even one week later.

Example 44

(Evaluation 1 on Viscosity of Hydrophobicized CNF Complex)

Samples were prepared wherein Hex-PEG-CNF (BB-C) were added in amounts of 1.0 to 2.0% relative to CY-5 (Example 44). Each of the samples was shaken and stirred, and then left stand for 5 minutes in a constant-temperature chamber (25° C.), and its viscosity was measured using a B-type viscometer (viscometer of TVB-15 model viscometer manufactured by Toki Sangyo Co., Ltd.), and a rotor No. M3 or M4 at a rotation speed of 12 rpm (the rotor No. M4 was used only in the 2.0% case).

TABLE 12

|  | Example44 | | |
| --- | --- | --- | --- |
| Hex-PEG-CNFs(BB-C) | 1.0% | 1.5% | 2.0% |
| CY-5 | 99.0% | 98.5% | 98.0% |
| viscosity 25° C. 12 rpm | 1140 | 6790 | 21040 |

As is seen at from Table 12, Hex-PEG-CNFs (BB-C) were confirmed to exert thickening effect.

The invention claimed is:

1. An oil thickener, comprising:
   surface-hydrophobicized cellulose nanofibers (CNFs),
   wherein the CNFs prior to being surface hydrophobicized have an average thickness of 3 to 200 nm and an average length of 0.1 μm or larger,
   wherein a 1 wt. % aqueous dispersion of the CNFs prior to being surface hydrophobicized have a viscosity of 700 to 2100 mPa·s measured at 25° C. using a B-type viscometer and a rotor No. M3 or M4 at a rotation speed of 12 rpm, and
   wherein hydroxyl groups in cellobiose units of the surface-hydrophobicized CNFs are esterified with vinyl esters and/or organic acid esters in a substitution degree of 0.2 to 0.8.

2. An oil thickener, comprising:
   surface-hydrophobicized cellulose nanofibers (CNFs),
   wherein the CNFs prior to being surface hydrophobicized have an average thickness of 3 to 200 nm and an average length of 0.1 μm or larger,
   wherein a 1 wt. % aqueous dispersion of the CNFs prior to being surface hydrophobicized have a viscosity of 300 to 10000 mPa·s measured at 25° C. using a B-type viscometer and a rotor No. M3 or M4 at a rotation speed of 12 rpm, and
   wherein hydroxyl groups in cellobiose units of the surface-hydrophobicized CNFs are esterified with vinyl esters and/or organic acid esters in a substitution degree of 0.2 to 0.8.

3. A hydrophobicized CNF complex, comprising:
   cellulose nanofibers (CNFs) which, prior to being surface hydrophobicized, have an average thickness of 3 to 200 nm and an average length of 0.1 μm or larger,
   wherein a 1 wt. % aqueous dispersion of the CNFs prior to being surface hydrophobicized have a viscosity of 300 to 10000 mPa·s measured at 25° C. using a B-type viscometer and a rotor No. M3 or M4 at a rotation speed of 12 rpm,
   wherein hydroxyl groups in cellobiose units of the surface-hydrophobicized CNFs are esterified with vinyl esters and/or organic acid vinyl esters, and the esterified CNFs are cross-linked together via a polyhydric alcohol and/or a polyalkylene glycol to form a complex, and/or the CNFs are bonded to part of the esterified CNFs to form a complex.

4. A hydrophobicized CNF complex obtained in a process comprising such steps that water-containing CNFs having an average thickness of 3 to 200 nm, which are obtained in such a manner that pulp having α-cellulose content of 60 to 99 wt. % is used as a polysaccharide, and a 0.5 to 10 wt. % aqueous mixture of the polysaccharide is jetted from a plurality of positions under a high pressure of 50 to 400 MPa to cause the plurality of jets to collide with each other to effect fibrillation, are added into an organic solvent together with potassium carbonate, and a polyhydric alcohol and/or a polyalkylene glycol, a cross-linking agent and a vinyl ester and/or an organic acid vinyl ester are added thereto, and the resulting mixture is allowed to react, and reaction product thus obtained is collected.

5. A hydrophobicized CNF complex for an oil thickener obtained in a process comprising such steps that water-containing CNFs having an average thickness of 3 to 200 nm, which are obtained in such a manner that pulp having α-cellulose content of 60 to 99 wt. % is used as a polysaccharide, and a 0.5 to 10 wt. % aqueous mixture of the polysaccharide is jetted from a plurality of positions under a high pressure of 50 to 400 MPa to cause the plurality of jets to collide with each other to effect fibrillation, are added into an organic solvent together with potassium carbonate, and a polyhydric alcohol and/or a polyalkylene glycol, a cross-linking agent and a vinyl ester and/or an organic acid vinyl ester are added thereto, and the resulting mixture is allowed to react, and reaction product thus obtained is collected.

6. An oil thickener composition in which at least the surface-hydrophobicized CNFs for an oil thickener according to claim 1 are incorporated.

7. An oil thickener composition in which at least the hydrophobicized CNF complex according to claim 3 is incorporated.

8. A cosmetic in which at least the surface-hydrophobicized CNFs for an oil thickener according to claim 1 are incorporated.

9. A cosmetic in which at least the hydrophobicized CNF complex according to claim 3 is incorporated.

10. An oil thickener composition in which at least the surface-hydrophobicized CNFs for an oil thickener according to claim 2 are incorporated.

11. An oil thickener composition in which at least the hydrophobicized CNF complex according to claim 4 is incorporated.

12. An oil thickener composition in which at least the hydrophobicized CNF complex for an oil thickener according to claim 5 is incorporated.

13. A cosmetic in which at least the surface-hydrophobicized CNFs for an oil thickener according to claim 2 are incorporated.

14. A cosmetic in which at least the hydrophobicized CNF complex according to claim 4 is incorporated.

15. A cosmetic in which at least the hydrophobized CNF complex for an oil thickener according to claim 5 is incorporated.

16. The oil thickener according to claim 1 wherein the vinyl esters and/or organic acid esters are selected from the group consisting of vinyl caproate, caprylic acid vinyl ester, vinyl caprate, lauric acid vinyl ester, and vinyl myristate.

17. The oil thickener according to claim 2 wherein the vinyl esters and/or organic acid esters are selected from the group consisting of vinyl caproate, caprylic acid vinyl ester, vinyl caprate, lauric acid vinyl ester, and vinyl myristate.

18. The hydrophobicized CNF complex according to claim 3 wherein the vinyl esters and/or organic acid esters are selected from the group consisting of vinyl caproate, caprylic acid vinyl ester, vinyl caprate, lauric acid vinyl ester, and vinyl myristate.

19. The hydrophobicized CNF complex according to claim 3 wherein a polyhydric alcohol and/or a polyalkylene glycol are bonded to a portion of the esterified CNFs to form a complex.

* * * * *